United States Patent
Schiller et al.

(10) Patent No.: US 11,737,997 B2
(45) Date of Patent: Aug. 29, 2023

(54) METHOD TO INCREASE CELLULAR AVAILABILITY OF CALCIUM IN SKIN CELLS AND MIXTURES

(71) Applicant: Merck Patent GmbH, Darmstadt (DE)

(72) Inventors: Alexander Paul Schiller, Darmstadt (DE); Lisa Eckelhoefer, Sessenbach (DE); Julia Bleifuss, Niedernberg (DE); Andrew Philip Salazar, Darmstadt (DE); Joerg von Hagen, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 376 days.

(21) Appl. No.: 16/795,779

(22) Filed: Feb. 20, 2020

(65) Prior Publication Data
US 2020/0405674 A1 Dec. 31, 2020

(30) Foreign Application Priority Data
Jun. 28, 2019 (EP) .................................. 19183370

(51) Int. Cl.
| A61K 31/198 | (2006.01) |
| A61K 33/06 | (2006.01) |
| A61K 31/4015 | (2006.01) |
| A61P 3/14 | (2006.01) |

(52) U.S. Cl.
CPC ........ A61K 31/198 (2013.01); A61K 31/4015 (2013.01); A61K 33/06 (2013.01); A61P 3/14 (2018.01)

(58) Field of Classification Search
CPC .................................................... A61K 31/198
See application file for complete search history.

(56) References Cited

U.S. PATENT DOCUMENTS

| 5,516,925 A | 5/1996 | Pedersen et al. |
| 8,425,956 B2 | 4/2013 | Thompson et al. |
| 8,795,705 B2 | 8/2014 | Voegel et al. |
| 2004/0086538 A1 | 5/2004 | Sauermann et al. |
| 2005/0249691 A1 | 11/2005 | Monks |
| 2008/0260672 A1 | 10/2008 | Oshimura et al. |

FOREIGN PATENT DOCUMENTS

| CH | 711092 A2 | 11/2016 |
| EP | 2404502 B1 | 4/2019 |
| KR | 10-2009-0054777 A | 6/2009 |
| WO | 0200185 A1 | 1/2002 |

(Continued)

OTHER PUBLICATIONS

Weinhaus et al. Mechanisms of arginine-induced increase in cytosolic calcium concentration in beta-cell line NIT-1. (Year: 1997).*

(Continued)

*Primary Examiner* — Sarah Alawadi
(74) *Attorney, Agent, or Firm* — Millen, White, Zelano & Branigan, PC; Ryan Pool

(57) ABSTRACT

The present invention relates to mixtures of serine or threonine together with at least one further amino acid or amino acid derivative and with at least one calcium salt or its hydrate and methods including this mixture including specific mixtures of such components and a formulations consisting of the mixture and a solvent.

6 Claims, 1 Drawing Sheet

(56) References Cited

FOREIGN PATENT DOCUMENTS

| WO | 07084932 A2 | 7/2007 |
|---|---|---|
| WO | 08142147 A1 | 11/2008 |
| WO | 17042748 A1 | 3/2017 |

OTHER PUBLICATIONS

Brian Bodemann. Ral G-Proteins and the Excocyst Complex are Mediators of the Cellular Response to Nutrients. (Year: 2011).*
Jessica Dauz Bihuniak. Mechanisms of dietary Protein-Induced Changes in Calcium Absorption Efficiency. (Year: 2014).*
Database GNPD [Online] MINTEL; Mar. 26, 2019 (Mar. 26, 2019), anonymous: "Moisture Anti-Aging Mist", XP055732272, retrieved from www.gnpd.com Database accession No. 6387437.
EP search report in corresponding EP application 20158663 dated Sep. 22, 2020 (pp. 1-9).
Tan et al., Feeding filaggrin: effects of l-histidine supplementation in atopic dermatitis, Clin. Cos. Invest. Dermatol., 2017, 10, 403 411.
Kim et al., Identification of the minimum region of flatfish myostatin propeptide (Pep45-65) for myostatin inhibition and its potential to enhance muscle growth and performance in animals, PLoS ONE, 2019, 14, 4.
Jokura et al., Molecular analysis of elastic properties of the stratum corneum by solid-state 13C-nuclear magnetic resonance spectroscopy. J. Invest. Dermatol., 1995, 104, 806-812.
Rawlings et al., Effect of lactic acid isomers on keratinocyte ceramide synthesis, stratum corneum lipid levels and stratum corneum barrier function, Arch. Dermatol. Res., 1996, 288, 383-390.
Harding et al., Dry skin, moisturization and corneodesmolysis., Int. J. Cos. Sci., 2000, 22, 21-52.
Rawlings et al., Moisturization and skin barrier function., Dermatologic Therapy, 2004, 17, 43-48.
Gad, Anti-aging effects of l-arginine, Journal of Advanced Research, 2010, 1, 169-177.
Fowler, Understanding the role of Natumal Morisurizing . . . ,Pract. Dermatol., 2012, 9, 36-40.
Souza et al., The in vivo effect of L-arginine on skin elasticity in mice, Braz. J. Pharm Sci., 2017, 53, 3, e00045.

* cited by examiner

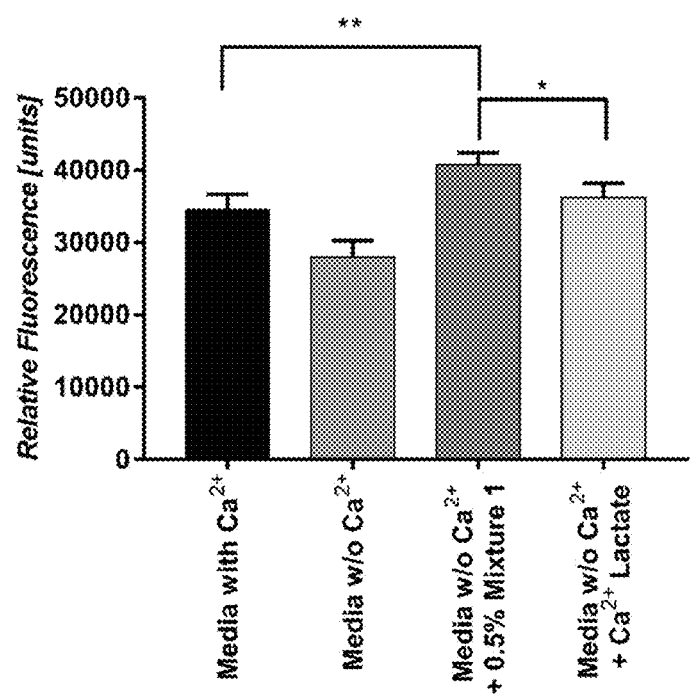

METHOD TO INCREASE CELLULAR AVAILABILITY OF CALCIUM IN SKIN CELLS AND MIXTURES

FIELD OF THE INVENTION

The present invention generally relates to the use of serine or threonine together with at least one further amino acid or amino acid derivative and with at least one calcium salt or its hydrate to increase cellular availability of calcium in living cells of the epidermis and to a specific mixture of such components and a formulation consisting of said mixture and a solvent.

BACKGROUND OF THE INVENTION

The epidermis, which is the outermost layer of the skin is primarily composed of keratinocytes. These cells differentiate upward form the basement membrane (*Stratum basale*), where they are in contact with the dermis, to form stratified layers which end as sheets of connected cornified cells at the outermost position. The epidermis is not directly supplied with nutrients via the circulatory system.

Through these layers of the epidermis, exists a calcium gradient. This gradient is low at the *Stratum basale* and gradually increases through the *Stratum spinosum*, with a sharp peak in the *Stratum granulosum*, and drops again in the outermost layer of the skin which is the *Stratum corneum*. Calcium is either present extracellularly or intracellularly, in the endoplasmic reticulum (ER) and is involved in multiple cellular process of the keratinocytes. With age, epidermal damage, and in disease conditions such as Darier disease and Hailey-Hailey disease, the calcium gradient is disrupted, which results in a dramatic change in the composition and functional ability of the epidermis. This even impacts the *Stratum corneum* since the proteins that hold together the building blocks of the *Stratum corneum* were formed in the living cells of the epidermis.

At a cellular level, calcium is involved in many processes such as keratinocyte differentiation, migration, and adhesion, as well as generating and maintaining epidermal junction proteins. In regular maintenance of the epidermis, calcium is involved in sustaining tissue integrity by controlling the formation of desmosomes as well as the formation and maintenance of the adhesive state of tight junction and cadherin proteins. Even in response to damage of the epidermis, calcium released primarily from the ER aids the repopulation of the epidermis with keratinocytes and restoration of the junction proteins. Thus, epidermal calcium flux is a dynamic process which requires calcium to be present in a cellularly available form that it may be stored intracellularly or harnessed in the appropriate physio-chemically process.

Epidermal shortages of calcium in age and/or disease need not to be alleviated by oral supplementation of calcium. In oral supplementation it is well known that calcium mineral salts exhibit poor aqueous solubility limiting their bioavailability.

Therefore, any attempts at topical supplementation or restoration of the calcium gradient in the epidermis would need to overcome the hurdles of solubility and bioavailability.

It is known from WO2007/084932 that amino acid chelated minerals have become well known for nutritional supplementation. The reported mixed amino acid/mineral compound includes a mineral bound by a first amino acid that is different from a second amino acid and is characterized as having increased solubility and/or increased absorption through the gastrointestinal (GI) tract compared to a compound with either only the first amino acid or the second amino acid.

U.S. Pat. No. 5,516,925 describes amino acid chelated mineral compositions containing amino acid ligands which have improved palatability.

WO02/00185 describes the use of calcium-releasing or binding substances for the specific attenuation or strengthening of the barrier function of the skin.

US2008/0260672 describes an aqueous preservative solution with a high amino acid content having particular preservative effect on fungi which is excellent in storage stability, and when incorporated in a cosmetic, is capable of imparting a high moisturizing effect without causing a sticky feeling, and imparting an effect of preventing dyed hair from color fading. Such compositions comprise pyrrolidone carboxylic acid and/or a salt thereof, a basic amino acid and/or a salt thereof, an acidic amino acid and/or a salt thereof, a neutral amino acid and/or a salt thereof and lactic acid and/or a salt thereof at a specific incorporation ratio and at a specific pH.

WO2008/142147 describes a composition comprising, in a physiologically acceptable carrier, pyrrolidone-5-carboxylic acid and at least one compound from citrulline, arginine and asparagine, in racemic or isomer form, and salts thereof, for the preparation of a medicament for use in the treatment and/or prevention of atopic dermatitis.

KR1020090054777 describes compositions comprising lactic acid or its salt, pyrrolidinone carboxylic acid or its salt and an amino acid for controlling pH of skin and cosmetics comprising the same. It is further reported that such compositions protect the skin barrier function and that ingredients of the composition are part of the natural moisturization factor (NMF). As a result, the reported compositions or cosmetics comprising such compositions are able to moisturize skin.

EP2404502 describes compositions containing pyrrolidone carboxylic acid and metallic salts, such as copper, zinc or manganese salts, which synergically potentiates the antiviral and antibacterial action of PCA.

WO2017/042748 describes a moisturizing cosmetic composition comprising at least one cosmetically acceptable salt of lactic acid, at least one amino acid selected from L-serine, glycine, leucine, lysine, proline, valine, tyrosine, glutamic acid, alanine, aspartic acid, arginine, tryptophan, histidine, phenylalanine, ornithine, threonine, and mixtures thereof, trehalose and at least one cosmetically acceptable salt of zinc.

Jokura Y et al, J Invest Dermatol 1995, 104, 806-812 investigates the elastic properties of the *Stratum corneum* by solid-state $^{13}$C-nuclear magnetic resonance spectroscopy.

Rawlings A. V. et al, Arch Dermatol Res 1996, 288, 383-390 describes the effect of lactic acid isomers on keratinocyte ceramide synthesis, *Stratum corneum* lipid levels and *Stratum corneum* barrier function.

Harding C et al, Int J Cos Sci 2000, 22, 21-52 reports an increased understanding of the desquamation process and provides new insights into the mode of action of moisturizing ingredients.

Rawlings A. V. et al, Dermatologic Therapy, 2004, 17, 43-48 describes *Stratum corneum* moisturization at a molecular level.

Gad M. Z., Journal of Advanced Research 2010, 1, 169-177 describes anti-aging effects of L-arginine.

Fowler J, Pract. Dermatol. 2012, 9, 36-40 describes components collectively called natural moisturizing factor (NMF) occurring naturally in the skin to treat xerotic, dry skin.

Souza Ad P B d et al, Braz J Pharm Sci 2017, 53(3) e00045 describes the in vivo effect of L-arginine on skin elasticity in mice.

Tan S P et al, Clin Cos Invest Dermatol 2017, 10, 403-411 investigates the effects of L-histidine supplementation in atopic dermatitis.

Kim J-H, Ahn B, Choi S-G, In S, Goh A R, Park S-G, et al, (2019) Amino acids disrupt calcium-dependent adhesion of *Stratum corneum*, PLoS ONE 14(4): e0215244 describe the $Ca^{2+}$ chelating property of amino acids, such as serine, and demonstrated that amino acids can interfere with the interaction of cadherins, separate *Stratum corneum* into pieces, and thereby stimulate the exfoliation process of skin.

However, there is still a need to bolster the existing calcium gradient particularly in aged skin and in disease conditions where this gradient is disrupted.

Consequently, it is an object of the present application to provide such a solution.

SUMMARY OF THE INVENTION

The present inventors have now found that the above object may be attained by the method described herein or the specific mixture of the present application.

The invention relates to the use of a combination of serine or threonine with at least one further amino acid or amino acid derivative and with at least one calcium salt or its hydrate to increase cellular availability of calcium in living cells of the epidermis, particularly living keratinocytes of the epidermis.

The invention relates further to a method for increasing cellular availability of calcium in living cells of the epidermis of a mammal, particularly of a human, comprising providing serine or threonine in combination with at least one further amino acid or amino acid derivative and with at least one calcium salt or its hydrate and applying said compounds, particularly as part of a cosmetic, dermatological, or pharmaceutical preparation or medical device, to the skin.

The invention relates further to a mixture consisting of serine, arginine, histidine, pyrrolidinone-5-carboxylic acid and at least one organic calcium salt or its hydrate.

The invention relates further to a formulation consisting of said mixture and a solvent.

DETAILED DESCRIPTION OF THE INVENTION

As disclosed before said combination of serine or threonine with at least one further amino acid or amino acid derivative and with at least one calcium salt or its hydrate enables the increase in cellular uptake capacity of calcium in living epidermal cells, particularly living keratinocytes, compared to the cellular uptake capacity of the calcium salt or its hydrate alone or even compared to the cellular uptake capacity of a combination of serine and one or more calcium salts or its/their hydrate(s).

Since calcium is supplied with the amino acids and/or amino acid derivatives, the calcium ions present in the skin are not disrupted and the preexisting calcium gradient remains intact. Due to its cellular availability of calcium, the cells are able to build up intra cellular stores of calcium in the ER which can then be used in the formation of desmosomes and cellular junction proteins. Said ability of the cells to harness this calcium is expressed by having a greater abundance of junction proteins and a stronger binding of epidermal cells to each other.

The amino acids, amino acid derivatives, calcium salts or their hydrates include all stereoisomers or racemic mixtures.

Preferably, serine is used instead of threonine. Particularly preferably L-serine is used instead of L-threonine.

The calcium salt or its hydrate to be used according to the invention is not limited and can be an inorganic or an organic calcium salt or an inorganic or an organic calcium hydrate.

Preferably, the at least one calcium salt or its hydrate is an organic calcium salt or its hydrate.

The invention therefore relates to the use as described before wherein the at least one calcium salt or its hydrate is an organic calcium salt or its hydrate.

Suitable calcium salts can be selected from calcium acetate, calcium aspartate, calcium ascorbate, calcium citrate, calcium gluconate, calcium lactate, calcium pidolate (calcium bis(5-oxo-L-prolinate), calcium alginate, or their hydrates, or a combination of these salts or hydrates including all stereoisomers or racemic mixtures.

The invention therefore relates to the use as described before or preferably described before wherein the at least one calcium salt or its hydrate is selected from calcium acetate, calcium aspartate, calcium ascorbate, calcium citrate, calcium gluconate, calcium lactate, calcium pidolate (calcium bis(5-oxo-L-prolinate), calcium alginate, or their hydrates, or a combination of these salts or hydrates.

Within said use as described before, 0.2 to 0.5 equivalents of calcium salt or hydrate shall be preferably used together with one equivalent of serine. Particularly preferably 0.3 to 0.4 equivalents of calcium salt or hydrate shall be preferably used together with one equivalent of serine when used according to the invention. It is particularly preferred to use molecular proportion of 1:0.33 of serine and the calcium salt or calcium hydrate when used according to the invention.

In a preferred embodiment of the invention, one calcium salt or one calcium hydrate is used as source for calcium ions in combination with serine or threonine and at least one further amino acid or amino acid derivative.

The invention therefore relates further to the use of a combination of serine or threonine with at least one further amino acid or amino acid derivative and with one calcium salt or its hydrate to increase cellular availability of calcium in living cells of the epidermis, particularly in living keratinocytes.

In a particular preferred embodiment of the invention, calcium L-lactate or its hydrates are used. A preferred hydrate of calcium L-lactate is calcium L-lactate pentahydrate.

The at least one further amino acid to be used according to the invention is not limited and can be any essential or non-essential amino acid known in the art.

In a preferred embodiment of the invention, the at least one further amino acid beside of serine or threonine is arginine and the other further amino acids or amino acid derivatives are not restricted.

The invention therefore relates to the use as described before or preferably described before wherein the at least further amino acid beside of serine or threonine is arginine.

In a preferred embodiment of the invention, the combination of amino acids and/or amino acid derivatives contains one, two, three, four or five further amino acids and one further amino acid derivative beside of serine or threonine.

It is preferred that the amount of serine or threonine is the highest amount within the combination of amino acids and/or amino acid derivatives to be used according to the invention.

The invention therefore relates to the use as described before or preferably described before wherein the combination of amino acids and/or amino acid derivatives contains one, two, three, four or five further amino acids and one further amino acid derivative beside of serine or threonine.

In another preferred embodiment of the invention, the combination of amino acids and/or amino acid derivatives contains one further amino acid and one further amino acid derivative beside of serine and arginine.

In another preferred embodiment of the invention, the combination of amino acids and/or amino acid derivatives contains two further amino acids and one further amino acid derivative beside of serine and arginine.

Further amino acids beside of serine or threonine and/or arginine are selected from histidine, cysteine, glutamic acid, or aspartic acid. Preferably, the further amino acid beside of serine and arginine is histidine.

Further amino acid derivatives are not limited and are known in the art. Suitable amino acid derivatives are L-homoserine, pyruvate, alpha-ketoglutarate, glutamate or L-glutamate, glutamine, L-glutamine, and pyrrolidinone-5-carboxylic acid and their isomeric forms.

Preferably, the further amino acid derivative is pyrrolidinone-5-carboxylic acid. Particularly preferably, the further amino acid derivative is L-pyrrolidinone-5-carboxylic acid.

It is preferred that the amount of the amino acid derivative, particularly L-pyrrolidinone-5-carboxylic acid is the second highest amount within the combination of amino acids and/or amino acid derivatives to be used according to the invention.

Preferably, all amino acids are used as racemic mixture. Particularly preferably, all amino acids are used as L-isomer.

Preferably, the amino acid derivative is used as L-isomer.

In a particular preferred embodiment of the invention, the combination of amino acids and amino acid derivatives comprises serine, arginine, histidine and pyrrolidinone-5-carboxylic acid, preferably L-pyrrolidinone-5-carboxylic acid, to be used together with a calcium salt or a preferred calcium salt as described before or preferably described before.

The invention therefore relates to the use as described before or preferably described before wherein the combination of amino acids and amino acid derivatives comprises serine, arginine, histidine and pyrrolidinone-5-carboxylic acid, preferably L-pyrrolidinone-5-carboxylic acid.

In a further particular preferred embodiment of the invention, the combination of amino acids and amino acid derivatives consists of serine, arginine, histidine and pyrrolidinone-5-carboxylic acid, preferably L-pyrrolidinone-5-carboxylic acid, to be used together with a calcium salt or a preferred calcium salt as described before or preferably described before.

The invention therefore relates to the use as described before or preferably described before wherein the combination of amino acids and amino acid derivatives consists of serine, arginine, histidine and pyrrolidinone-5-carboxylic acid, preferably L-pyrrolidinone-5-carboxylic acid.

The invention therefore relates to the use as described before or preferably described before wherein the combination of amino acids and amino acid derivatives consists of L-serine, L-arginine, L-histidine and L-pyrrolidinone-5-carboxylic acid.

The described use to increase cellular availability of calcium in living epidermal cells is preferably performed by using a specific mixture which is able to be incorporated in a cosmetic, dermatological, or pharmaceutical composition or medical device to be applied topically on the epidermis of mammals, preferably on the epidermis of humans.

The invention therefore relates further to a mixture consisting of serine, arginine, histidine, pyrrolidinone-5-carboxylic acid and at least one organic calcium salt or its hydrate which is a preferred embodiment to be used according to the invention increasing the cellular availability of calcium in living cells of the epidermis, preferably in living keratinocytes of the epidermis.

Preferably, the mixture according to the invention contains L-pyrrolidinone-5-carboxylic acid.

Preferably, the mixture according to the invention contains L-serine, L-arginine and L-histidine.

Preferably, the mixture according to the invention or one of the preferred embodiments of said mixture contains the at least one organic calcium salt or its hydrate selected from calcium acetate, calcium aspartate, calcium ascorbate, calcium citrate, calcium gluconate, calcium lactate, calcium pidolate (calcium bis(5-oxo-L-prolinate), calcium alginate, or their hydrates, or a combination of these salts or hydrates including all stereoisomeric forms.

The invention therefore relates to a mixture as described before or preferably described before wherein the calcium salt or its hydrate is selected from calcium acetate, calcium aspartate, calcium ascorbate, calcium citrate, calcium gluconate, calcium lactate, calcium pidolate (calcium bis(5-oxo-L-prolinate), calcium alginate, or their hydrates, or a combination of these salts or hydrates.

Preferably, the mixture according to the invention contains one calcium salt or its hydrate.

In a preferred embodiment of the invention, the one calcium salt is calcium lactate or its hydrates. A preferred calcium lactate is calcium L-lactate.

In a particular preferred embodiment of the invention, the calcium salt is calcium L-lactate hydrate where calcium L-lactate pentahydrate is particularly preferred.

The invention therefore relates to a mixture consisting of serine, arginine, histidine, pyrrolidinone-5-carboxylic acid and calcium lactate hydrate.

The invention therefore relates preferably to a mixture consisting of L-serine, L-arginine, L-histidine, L-pyrrolidinone-5-carboxylic acid and calcium L-lactate pentahydrate.

Within said described mixture, serine is preferably contained in 25 to 35% by weight, arginine is preferably contained in 5 to 10% by weight, histidine is preferably contained in 5 to 10% by weight, pyrrolidinone-5-carboxylic acid is preferably contained in 10 to 30% by weight and the calcium salt or hydrate is preferably contained in 25 to 35% by weight, wherein the combined total amounts add to 100% by weight.

Within said described and preferred mixture, L-serine is preferably contained in 25 to 35% by weight, L-arginine is preferably contained in 5 to 10% by weight, L-histidine is preferably contained in 5 to 10% by weight, L-pyrrolidinone-5-carboxylic acid is preferably contained in 10 to 30% by weight and the calcium L-lactate pentahydrate is preferably contained in 25 to 35% by weight, wherein the combined total amounts add to 100% by weight.

The invention therefore relates to the mixture as described before or preferably described before, wherein serine is contained in 25 to 35% by weight, arginine is contained in 5 to 10% by weight, histidine is contained in 5 to 10% by weight, pyrrolidinone-5-carboxylic acid is contained in 10 to 30% by weight and the calcium salt or hydrate is contained in 25 to 35% by weight, wherein the combined total amounts add to 100% by weight.

As described before, 0.2 to 0.5 equivalents of calcium salt or hydrate shall be preferably combined with one equivalent of serine. Particularly preferably 0.3 to 0.4 equivalents of calcium salt or hydrate, as described before or preferably described before, shall be preferably combined with one equivalent of serine or L-serine within the mixture according to the invention. It is particularly preferred to use molecular proportion of 1:0.33 of serine and the calcium salt or calcium hydrate in the mixture according to the invention. It is particularly preferred to use molecular proportion of 1:0.33 of L-serine and calcium L-lactate pentahydrate in the mixture according to the invention.

It is preferred that the amount of serine or L-serine is the highest amount within the combination of amino acids and amino acid derivative in the mixture according to the invention.

It is further preferred that the amount of pyrrolidinone-5-carboxylic acid or L-pyrrolidinone-5-carboxylic acid is the second highest amount within the combination of amino acids and amino acid derivative in the mixture according to the invention.

A particularly preferred mixture according to the invention consists of 29% to 31% by weight of L-serine, 7% to 8% by weight of L-arginine, 7% to 8% by weight of L-histidine, 20% to 25% by weight of L-pyrrolidinone-5-carboxylic acid, and 29% to 31% by weight of calcium L-lactate pentahydrate.

A further particularly preferred mixture according to the invention consists of 30.6% by weight of L-serine, 7.5% by weight of L-arginine, 7.3% by weight of L-histidine, 24.2% by weight of L-pyrrolidinone-5-carboxylic acid, and 30.4% by weight of calcium L-lactate pentahydrate.

The described mixture or preferably described mixture is preferably a powder mixture.

The invention therefore relates to the mixture as described before or preferably described before which is a powder mixture. Said mixture is further characterized in that its aqueous solubility is high.

Nevertheless, said mixture may be incorporated alternatively as a formulation together with a solvent into a cosmetic, dermatological, pharmaceutical composition or medical device.

The invention therefore relates further to a formulation consisting of a mixture according to the invention and a solvent.

The type of solvent is not restricted but polar solvents are preferred, such as water or a mixture of an alcohol and water. Suitable alcohols may be selected from methanol, ethanol, 1,2-ethanediol, 1-propanol, 2-propanol, 1,2-propanediol, 1-3-propanediol, 1-butanol, 2-butanol, 3-butanol, 1,4-butanediol, 1,3-butanediol, and 1,2-butanediol.

Beside of the described advantage by using the mixture according to the invention, such as the increase in cellular uptake capacity of calcium in living epidermal cells, particularly living keratinocytes, expressed by having a greater abundance of junction proteins and a stronger binding of epidermal cells to each other, all other advantages of the single ingredients or of a mixture of said components known in the art remain. Such advantages known in the art are the moisturizing ability, the strengthening of skin barrier function and control of pH of skin and cosmetics and antiviral and antibacterial action.

The mixture according to the invention improves the binding of the corneocytes by making calcium available to living cells in the epidermis where the desmosomes are formed. In addition, it is found that the mixture according to the invention also improves the hydration of the *Stratum granulosum*, enabling the enzymatic processing of the desmosomes to corneodesmosomes. The cellularly available calcium also allows for the formation and maintenance of classical and non-classical cadherins as well as the tight junction proteins. It is further found that the mixture according to the invention alters the cytoskeleton of the living keratinocytes in the epidermis.

Combination of the mixture as described before or preferably described before, with other active ingredients to further support such advantages in a cosmetic, dermatological, or pharmaceutical composition or medical device is advantageous.

Particularly suitable active ingredients for combination are humectants. Suitable humectants to be used together with the mixture according to the invention in a cosmetic, dermatological, or pharmaceutical composition or medical device are ectoine (RonaCare® Ectoin), hydroxyectoine, trehalose, glycerol, glycosyl glycerol, β-mannosyl glycerate (firoin), β-mannosylglyceramide (firoin A), di-myo-inositol phosphate (DIP), cyclic 2,3-diphosphoglycerate (cDPG), 1,1-diglycerol phosphate (DGP), dimannosyl diinositol phosphate (DMIP), betaine, glycine betaine, proline betaine, glutamate betaine, alanine, proline, glutamine, N-acetyl lysine, glutamine 1-amide, taurine, choline, choline O-sulfate, carnitine, arsenobetaine, crotonobetaine, dimethyl sulfonioacetate, dimethyl sulfopropionate, homobetaine, trimethylamine N-oxide, panthenol, sorbitol, meglumine, hyaluronic acid or hyaluronic acid derivatives, urea (RonaCare® Urea) and niacinamide (RonaCare® Nicotinamide).

For the purposes of the present invention, the term "composition" is also used synonymously alongside the term "preparation".

The preparations here are usually preparations which can be applied topically, such as, for example, cosmetic or dermatological preparations or medical devices. "Can be applied topically" means that the preparation is applied externally and locally, i.e. that the preparation must be suitable, for example, for being able to be applied to the skin. In this case, the preparations comprise a cosmetically, pharmaceutically or dermatologically suitable vehicle and, depending on the desired property profile, optionally further suitable ingredients. The topical preparations are preferably employed as cosmetic or dermatological composition, particularly preferably as cosmetic composition. Suitable vehicles and assistants or fillers are described in detail in the following part.

The preparations may include or comprise, essentially consist of or consist of the necessary or optional constituents mentioned above and/or below. All compounds or components which can be used in the preparations are either known and commercially available or can be synthesised by known processes.

The mixture according to the invention, as described before or as preferably described before is employed in the topical preparations in amounts of 0.01 to 10% by weight, preferably in amounts of 0.05 to 10% by weight, particularly preferably in amounts of 0.1% by weight to 5% by weight and very particularly preferably in amounts of 0.5 to 3% by weight, based on the total amount of the preparation. The person skilled in the art is presented with absolutely no difficulties here in selecting the amounts appropriately depending on the intended action of the preparation.

Furthermore, the topical preparations may comprise at least one further humectant as further ingredient as described before. Such further humectant(s) is/are preferably present in the topical preparation in an amount of 0.01 to 20% by weight, particularly preferably in an amount of 0.1 to 15% by weight and very particularly preferably in an amount of 0.2 to 8% by weight, based on the total amount of the preparation.

Besides the mixture according to the invention, as described above or described as preferred, the preparations may additionally also comprise at least one UV filter.

Organic UV filters, so-called hydrophilic or lipophilic sun-protection filters, are effective in the UVA region and/or UVB region and/or IR and/or VIS region (absorbers). These substances can be selected, in particular, from dibenzoylmethane derivatives, cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO-93/04665. Further examples of organic filters are indicated in the patent application EP-A 0 487 404. The said UV filters are usually named below in accordance with INCI nomenclature.

Particularly suitable for a combination with the mixture according to the invention are Ethylhexyl salicylate, Phenylbenzimidazoiesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid. Disodium phenyldibenzimidazoletetrasulfonate, Methylenebis(benzotriazolyl)tetramethylbutylphenol, Butyl Methoxydibenzoylmethane, Ethylhexyl Triazone. Diethylhexyl Butamido Triazone, Drometrizole trisiloxane, Phenylene bis-diphenyl-triazine, Polysilicone-15, 1,1-Dicarboxy(2,2'-dimethylpropyl)-4,4-diphenylbutadiene, 2,4-bis[5-1 (dimethylpropyl) benzoxazol-2-yl(4-phenyl) imino]-6-(2-ethylhexyl)imino-1, 3,5-triazine and mixtures thereof. These organic UV filters are generally incorporated into preparations in an amount of 0.01% by weight to 20% by weight, preferably 1% by weight to 10% by weight.

Besides the mixture according to the invention, humectants and/or the optional organic UV filters, as described above, the preparations may comprise further inorganic UV filters, so-called particulate UV filters.

The following examples are also encompassed by the present disclosure and may fully or partly be incorporated into embodiments.

Preference is given here both to those from the group of the titanium dioxides, such as, for example, coated titanium dioxide (for example Eusolex® T-2000, Eusolex®T-AQUA, Eusolex®T-AVO, Eusolex®T-PRO, Eusolex® T-EASY), zinc oxides (for example Sachtotec®), iron oxides or also cerium oxides and/or zirconium oxides.

It may furthermore be preferred for the preparations to comprise inorganic UV filters which have been aftertreated by conventional methods, as described, for example, in Cosmetics & Toiletries, February 1990, Vol. 105, pp. 53 64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerine.

These inorganic UV filters are generally incorporated into the preparations in an amount of 0.1% by weight to 25% by weight, preferably 2% by weight to 10% by weight.

By combination of one or more of the said compounds having a UV filter action, the protective action against harmful effects of the UV radiation inducing photo-ageing can be optimised.

All said UV filters can also be employed in encapsulated form. In particular, it is advantageous to employ organic UV filters in encapsulated form.

The capsules in said topical preparations are preferably present in amounts which ensure that the encapsulated UV filters are present in the preparation in the percent by weight ratios indicated above.

The preparations described, which in accordance with the invention comprise the mixture as described before or preferably described before, may furthermore also comprise coloured pigments, where the layer structure of the pigments is not limited.

The coloured pigment should preferably be on use of 0.5% by weight to 5% by weight. The selection of a corresponding pigment is familiar to the person skilled in the art.

Further preparations comprising the mixture as described before or preferably described before may likewise comprise at least one further cosmetic active compound, for example selected from antioxidants, anti-ageing, anti-wrinkle, anti-dandruff, anti-acne, anti-cellulite active compounds, deodorants or vitamins.

The protective action of said preparations against oxidative stress or against the effect of free radicals can be improved if the preparations comprise one or more antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysta sulfoximine, buthionine sulfones, penta-, hexa- and heptathionine sulfoximine) in very low tolerated doses (for example pmol to μmol/kg), and also (metal) chelating agents, (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA, pentasodium ethylenediamine tetramethylene phosphonate and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are also compounds of the formulae A or B

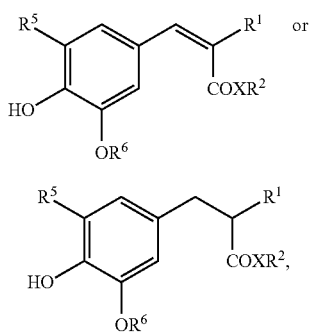

in which $R^1$ can be selected from the group —$C(O)CH_3$, —$CO_2R^3$, —$C(O)NH_2$ and —$C(O)N(R^4)_2$, X denotes O or NH,'

$R^2$ denotes linear or branched alkyl having 1 to 30 C atoms, $R^3$ denotes linear or branched alkyl having 1 to 20 C atoms, $R^4$ in each case, independently of one another, denotes H or linear or branched alkyl having 1 to 8 C atoms, $R^5$ denotes H, linear or branched alkyl having 1 to 8 C atoms or linear or branched alkoxy having 1 to 8 C atoms and $R^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene) malonate (for example Oxynex® ST Liquid) and/or bis (2-ethylhexyl) 2-(4-hydroxy-3,5-dimethoxybenzyl) malonate (for example RonaCare® AP).

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such preparations with the mixture according to the invention in percent by weight ratios in the range from 1000:1 to 1:1000, preferably in percent by weight ratios of 100:1 to 1:100.

Suitable anti-ageing active compounds, in particular for skin-care preparations, are products from Merck, such as, for example, 5,7-dihydroxy-2-methylchromone, marketed under the trade name RonaCare®Luremin®, or the commercial products RonaCare®ASCIII®, RonaCare®RenouMer, RonaCare®VTA, RonaCare®Poppy SE, RonaCare®Isoquercetin or RonaCare®Cyclopeptide 5.

The preparations to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the mixture according to the invention in ranges from 0.01% by weight to 5.0% by weight, based on the total weight.

The retinoids described are at the same time also effective anti-cellulite active compounds. A likewise known anti-cellulite active compound is caffeine.

The preparations may preferably comprise assistants, such as, for example, cosmetic oils (for example Caprylic/ Capric Triglycerides, C12-15 alkyl Benzoate, isopropyl myristate, arylalkyl benzoates, such as, for example, phenethyl benzoate (X-Tend 226) or oil components of the Cosmacol brand, such as Dimyristyl Tartrate, Tri C14-C15 Alkyl Citrate, C12-C13 Alkyl Lactate, Tridecyl Salicylate, C12-C13 Alkyl Octanoate, C12-C13 Alkyl Malate, C12-C13 Alkyl Citrate, C12-C13 Alkyl Tartrate), or polar-protic assistants (for example propylene glycol, glycerol, isopropanol, ethanol) or so-called solubilisers (for example Butylphthalimide, Isopropylphthalimide, Dimethylisosorbide). Very particularly preferred cosmetic oils are C12-C13 Alkyl Lactate, commercially available as Cosmacol ELI and phenethyl benzoate, commercially available as X-Tend 226.

The preparations as described before may be synthesized in that the mixture according to the invention or the formulation according to the invention is mixed with a vehicle which is suitable for such preparations and optionally with assistants and or fillers. Suitable vehicles and assistants or fillers are described in detail in the following part.

The said constituents of the preparation can be incorporated in the usual manner, with the aid of techniques which are well known to the person skilled in the art.

Preparations suitable for external use, for example can be applied or sprayed onto the skin as cream or milk (O/W, W/O, O/W/O, W/O/W), as lotion or emulsion, in the form of oily-alcoholic, oily-aqueous or aqueous-alcoholic gels or solutions. They can be in the form of solid sticks or formulated as aerosol. They can be in the form of shampoo, shower gel, cleansing milk or serum.

The following, for example, may be mentioned as application form of the preparations to be employed: solutions, suspensions, emulsions, PIT emulsions, pastes, ointments, gels, creams, lotions, powders, oils, aerosols plasters, compresses, bandages and sprays.

Preferred assistants originate from the group of preservatives, stabilisers, solubilisers, colorants, odour improvers, thickeners, plasticisers, humectants, interface-active agents, emulsifiers, preservatives, antifoaming agents, perfumes, waxes, lanolin, propellants and other ingredients usually used in cosmetics.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, XTend 226, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type. Emulsifiers that can be used are, for example, known W/O and O/W emulsifiers. It is advantageous to use further conventional co-emulsifiers in preferred O/W emulsions.

Preferred oils and/or lipids for said topical preparations include: paraffin, isoparaffin, dicaprylyl ether, PPG-15, stearyl ether, beeswax, candelilla wax, carnauba wax, ethylhexyl stearate, caprylic/capric triglycerides, cetyl lactate, stearyl stearate, isononyl isononanoate, octyldodecanol, hexyldecanol, squalene, natural triglycerides such as cherry kernel oil (*Prunus Cerasus*), *Persea Gratissima* oil, *Carthamus Tinctorius* seed oil, *Macadamia Temifolia* seed oil, cocoa butter (*Theobroma Cacao*), *Butyrospermum Parkii* butter and mixtures thereof.

Preferred absorbing and/or texturizing agents for said preparations include modified maize starch, silica, talc, zinc stearate, magnesium sulfate, zinc oxide, calcium and aluminium borosilicate, starches and derivatives, polyurethanes, and mixtures thereof.

The invention relates further to a method for the cosmetic treatment of the skin of a mammal, preferably a human, comprising a step of applying a cosmetic preparation comprising a mixture as described above to the skin thus enabling an increase in cellular availability of calcium in living cells of the epidermis.

The application is carried out using standard techniques, for example by the application of shampoo, shower gel, cream, cleansing milk, paste, gel, lotion, serum to the skin to be treated, or the dissolution of predetermined amount of the preparation comprising the mixture as described before or the mixture as such as described before in water and the subsequent use of said water thus admixed or of the foam formed for cleansing or skin treatment.

In a further aspect, the invention relates further to a method for the dermatological or pharmaceutical treatment of the skin of a mammal, preferably a human, comprising a step of applying a dermatological or pharmaceutical preparation comprising a mixture as described above to the skin thus enabling an increase in cellular availability of calcium in living cells of the epidermis for restoring and repair of the disrupted calcium gradient caused by a disease and/or by age.

The application is carried out using standard techniques as explained for the cosmetic treatment and applies accordingly.

In a further aspect, the invention relates to a method for the treatment of the skin of a mammal, preferably a human, comprising a step of applying a medical device comprising a mixture as described above, preferably in form of a topical preparation or as part of a kit of parts or as part of a container, to the skin thus enabling an increase in cellular availability of calcium in living cells of the epidermis as described before.

The application is carried out using standard techniques as explained before.

According to a further aspect, the invention relates to a cosmetic, dermatological, pharmaceutical product or medical device comprising a) a container delimiting a least one compartment closed by a respective closure element and b) a cosmetic, dermatological, or pharmaceutical preparation comprising the mixture as described before, or comprising serine or threonine, at least one further amino acid or amino acid derivative, and at least one calcium salt or its hydrate having the actions as describe before, arranged within said compartment.

The container may have any appropriate form. It may in particular be in the form of a bottle, a tube, a capsule, a can, a jar, a box or a bag.

The closure element may be in the form of a removable stopper, lid, ribbon, or tearing sheet. It may also be in the form of a dispensing element, in particular a pump, a valve or a cap with a spray nozzle. The closure element may be coupled to the container in any way known in the art, such as by a screw, bayonet, snap coupling, by welding, gluing or by magnetic attraction. The material of the container is not limited in any way but shall have no influence on the stability of the contained preparation able to be topically applied. Suitable materials are plastic materials, such as polypropylene or polyethylene, glass, metal or metal alloy.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

The technical teaching disclosed with the present invention may be abstracted and combined with other examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. EP 19183370.6, filed Jun. 28, 2019 are incorporated by reference herein.

EXAMPLES

Example 1: Cell Culture and Assaying Cellular Availability of Calcium

The mixture used in this example consists of the following ingredients as disclosed in table 1. Said mixture is named Mixture 1 in the following.

TABLE 1

| Ingredient | Article number | CAS No | Conc. [g/Kg] |
|---|---|---|---|
| L-serine | 107647 | 56-45-1 | 306.45 |
| L-arginine | 101587 | 74-79-3 | 74.60 |
| L-histidine | 104352 | 71-00-1 | 72.58 |
| L-PCA | 83160 Aldrich | 98-79-3 | 241.94 |
| Ca L-Lactate•5H$_2$O | 102102 | 5743-47-5 | 304.44 |
| | | Total | 1000 |

PCA = pyrrolidinone-5-carboxylic acid

Cell Culture and Treatment

HaCaT skin keratinocytes are cultured in DMEM without calcium (Thermo Fisher, art. no. 21068028) supplemented with 10% FBS until 80% confluency for a minimum of three passages. The cells are then seeded into a 96 well plate at a density of 1.25×10$^5$ cells/mL and incubated under the same conditions for 24 hours. Next, the culture media is removed, cells are washed with phosphate buffered saline, and are further incubated 24 hours with DMEM without calcium and without the addition of supplements. After this, cells are treated for 30 min with calcium free culture media, commercially available calcium containing culture media (Thermo Fisher, art. no. 11995123), calcium free culture media DMEM supplemented with 0.5% of Mixture 1, and calcium free culture media DMEM supplemented with calcium L-lactate pentahydrate at an equimolar concentration as present in 0.5% of Mixture 1. Ionomycin (7 μM; 50 μL) and the dye 2× Fluo-4 Direct™ calcium reagent (50 μL) are then added to all of the samples. Cells are incubated for 60 min at room temperature and then measured spectrophotometrically at Ex/Em of 485±20 nm/535±25 nm by using Tecan 20M spark. Baseline is defined as cells treated with calcium free culture media without the addition of ionomycin.

Statistical significance is assessed by performing a one-way ANOVA with Turkey's multiple comparison test to compare conditions to each other.

(The FIGURE: * p<0.05, ** p<0.01). All experiments are performed in triplicates.

Interference in the assessment of cellularly available calcium from intracellular sources is accounted for by culturing the cells in calcium free cell culture media for a minimum of three passages and also starving the cells of serum for 24 hours. Ionomycin (7 μM) is used to open the calcium channels of cells enabling its uptake. This makes it possible to assess the maximum cellular availability of calcium to cells in one hour.

Result

The FIGURE shows the relative fluorescence of the measured media.

From these data, the cells treated with 0.5% Mixture 1 show the highest fluorescence signal in the assay implying greatest cellular availability of calcium to these cells when compared to the other samples. The significant difference to the condition where only calcium L-lactate pentahydrate is provided to the cells documents that the other components of Mixture 1 facilitate the cellular uptake of calcium in keratinocytes.

Example 2: Cell Culture and Formation and Maintenance of the Adhesive State of Tight Junction and Cadherin Proteins HaCat cells which are a human epidermal keratinocyte celline adapted to grow in DMEM media without calcium (Thermo Fisher, art. no. 21068028) are seeded onto coverslips in a 6 well plate for 24 hours at 37° C., 5% CO$_2$. After this the cells are treated with Mixture 1 for 48 hours and incubated under the same conditions. The cells are then fixed and stained using a standard immunofluorescence protocol (based on J. E. Gautrot et al, Biomaterials 33 (2012) 5221-5229) using commercially available primary antibodies against CDH3, CDH11, or occludin (R&D systems, Germany). CDH3 is representative for a classical cadherin and CDH11 is representative for a non-classical cadherin. Occludin is used to exemplify tight junction proteins. A Donkey Anti-Rabbit IgG NorthernLights™ NL557-conjugated antibody is used as a secondary anti-body for detection (R&D systems, Germany). Actin filaments are stained using FITC conjugated phalloidin (Sigma-Aldridge, USA). Actin filaments are stained to visualize changes in the cytoskeleton. Imaging (confocal microscopy) is performed using a SP8 confocal laser scanning microscope (Leica, Germany).

Result:

An increase in the abundance of CDH3, CDH11, and Occludin is observed when cells are treated with Mixture 1 when compared to untreated cells. Alteration in the cytoskeleton is also observed, indicating reorganization of cells to increased cellular contact and allowing the cells to build intra cellular junction.

Formulation Examples

Example 1: O/W Cream

| Ingredients | | INCI (CTFA) | [%] |
|---|---|---|---|
| A | | | |
| Montanov 68 | (1) | CETEARYL ALCOHOL, CETEARYL GLUCOSIDE | 4.00 |
| Lanette ® O | (2) | CETEARYL ALCOHOL | 1.00 |
| Span 60 | (3) | SORBITAN STEARATE | 1.50 |
| Isopropyl Palmitate | (2) | ISOPROPYL PALMITATE | 3.00 |
| Cetiol ® CC | (2) | DICAPRYLYL CARBONATE | 3.00 |
| Lanol 99 | (1) | ISONONYL ISONONANOATE | 3.00 |

-continued

| Ingredients | | INCI (CTFA) | [%] |
|---|---|---|---|
| B | | | |
| Water, demineralized | | AQUA (WATER) | ad 100 |
| 1,2-Propanediol | (4) | PROPYLENE GLYCOL | 3.00 |
| Rhodicare XC | (5) | XANTHAN GUM | 0.30 |
| C | | | |
| Euxyl ® PE 9010 | (6) | PHENOXYETHANOL, ETHYLHEXYL GLYCERIN | 1.00 |
| D | | | |
| Mixture 1 | (4) | SERINE, CALCIUM LACTATE, PCA, ARGININE, HISTIDINE | 1.00 |
| Citric acid anhydrous | (4) | CITRIC ACID | 0.10 |
| tri-Sodium Citrate-Dihydrate | (4) | SODIUM CITRATE | 4.73 |
| Water, demineralized | | AQUA (WATER) | 15.00 |

Procedure:

Disperse Xanthan Gum in water phase. Heat phases A and B to 75° C. Stir phase A into phase B. Homogenize. Cool down to room temperature and add phases C and D.

Sources of Supply:

(1) Seppic; (2) BASF SE; (3) Croda; (4) Merck KGaA, Darmstadt, Germany/EMD Performance Materials; (5) Azelis Germany GmbH; (6) Schillke & Mayr GmbH.

Example 2: Face Cream (O/W)

| Ingredients | | INCI (CTFA) | [%] |
|---|---|---|---|
| A | | | |
| Montanov 202 | (1) | ARACHIDYL ALCOHOL, BEHENYL ALCOHOL, ARACHIDYL GLUCOSIDE | 3.00 |
| Lanol 99 | (1) | ISONONYL ISONONANOATE | 2.00 |
| Miglyol ® 812 N | (2) | CAPRYLIC/CAPRIC TRIGLYCERIDE | 2.00 |
| Cetiol ® CC | (3) | DICAPRYLYL CARBONATE | 3.00 |
| Cocoate BG | (4) | BUTYLENE GLYCOL COCOATE | 2.00 |
| B | | | |
| Water, demineralized | | AQUA (WATER) | ad100 |
| C | | | |
| Simulgel NS | (1) | HYDROXYETHYL ACRYLATE/SODIUM ACRYLOYLDIMETHYLTAURATE COPOLYMER, SQUALANE, POLYSORBATE 60 | 2.00 |
| D | | | |
| RonaCare ® Isoquercetin | (5) | ISOQUERCETIN | 0.50 |
| 1,2-Propanediol | (5) | PROPYLENE GLYCOL | 10.00 |
| E | | | |
| Preservatives (q.s.) | | | 0.00 |
| Mixture 1 | | SERINE, CALCIUM LACTATE, PCA, ARGININE, HISTIDINE | 1.00 |

Procedure:

Combine phases A and B separately and heat to 80° C. Add phase A to phase B while stirring. Homogenize. Add phase C at ~60° C. Add dissolved phase D (warm up to 40-50° C.). Add phase E at 40° C. and adjust pH to 5.0-5.5 with sodium hydroxide.

Sources of Supply:

(1) Seppic; (2) 101 Oleo GmbH; (3) BASF SE; (4) Gattefossé (Deutschland) GmbH; (5) Merck KGaA, Darmstadt, Germany/EMD Performance Materials Example 3: W/O Emulsion

| Ingredients | | INCI (CTFA) | [%] |
|---|---|---|---|
| A | | | |
| RonaCare ® Ectoin | (1) | ECTOIN | 0.50 |
| RonaCare ® Magnesium Sulfate | (1) | MAGNESIUM SULFATE | 1.20 |
| 1,2-Propanediol | (1) | PROPYLENE GLYCOL | 4.00 |
| Water, demineralized | | AQUA (WATER) | ad100 |
| B | | | |
| Dermofeel ® PGPR | (2) | POLYGLYCERYL-3 POLYRICINOLEATE | 3.00 |
| Cetiol ® J 600 | (3) | OLEYL ERUCATE | 10.00 |
| Tegosoft ® DC | (4) | DECYL COCOATE | 10.00 |
| Beeswax yellow | (5) | CERA ALBA (BEESWAX) | 0.50 |
| Lameform TGI | (3) | POLYGLYCERYL-3 DIISOSTEARATE | 2.00 |
| C | | | |
| Preservatives (q.s.) | | | 0.00 |
| Mixture 1 | | SERINE, CALCIUM LACTATE, PCA, ARGININE, HISTIDINE | 1.00 |

Procedure:

Heat phases A and B to 75° C. Stir phase A into phase B. Homogenize. Cool down while stirring. Add ingredients of phase C.

Sources of Supply:

(1) Merck KGaA, Darmstadt, Germany/EMD Performance Materials; (2) Dr. Straetmans; (3) BASF SE; (4) Evonik Nutrition & Care GmbH; (5) Gustav Heess GmbH Example 4: Sun Lotion with SPF 15

| Ingredients | | INCI (CTFA) | [%] |
|---|---|---|---|
| A | | | |
| Eusolex ® OCR | (1) | OCTOCRYLENE | 10.00 |
| Eusolex ® 9020 | (1) | BUTYL METHOXYDIBENZOYLMETHANE (AVOBENZONE) | 3.00 |
| Tegosoft ® TN | (2) | C12-15 ALKYL BENZOATE | 9.90 |
| Lanette ® O | (3) | CETEARYL ALCOHOL | 2.00 |
| B | | | |
| Water, demineralized | | AQUA (WATER) | ad100 |
| Glycerol, anhydrous | (1) | GLYCERIN | 2.00 |
| Complexing agent (q.s.) | | | 0.00 |
| B1 | | | |
| Veegum Ultra | (4) | MAGNESIUM ALUMINUM SILICATE | 0.40 |
| Keltrol ® CG-RD | (5) | XANTHAN GUM | 0.10 |
| B2 | | | |
| Emulsiphos | (6) | POTASSIUM CETYL PHOSPHATE, HYDROGENATED PALM GLYCERIDES | 3.00 |

-continued

| Ingredients | INCI (CTFA) | [%] |
|---|---|---|
| C | | |
| Preservatives (q.s.) | | 0.00 |
| Mixture 1 | SERINE, CALCIUM LACTATE, PCA, ARGININE, HISTIDINE | 1.00 |

Procedure:

Combine Phase A and B separately. Add Phase B1 to B while stirring. Stir until a homogeneous phase is obtained. Add phase B2 and heat phase A and B to 70-75° C.

Add phase A without stirring to phase B and homogenize.

Cool down while stirring, add phase C and adjust pH to 5.5-6.

Homogenize.

Source of Supply:

(1) Merck KGaA, Darmstadt, Germany/EMD Performance Materials; (2) Evonik Nutrition & Care GmbH; (3) BASF SE; (4) R. T. Vanderbilt Company Inc; (5) RAHN GmbH; (6) Symrise

Example 5: (W/Si) Emulsion

| Ingredients | | INCI (CTFA) | [%] |
|---|---|---|---|
| A | | | |
| RonaCare ® Ectoin | (1) | ECTOIN | 1.00 |
| RonaCare ® Allantoin | (1) | ALLANTOIN | 0.15 |
| RonaCare ® Sodium Chloride | (1) | SODIUM CHLORIDE | 2.00 |
| 1,2-Propanediol | (1) | PROPYLENE GLYCOL | 5.00 |
| Germaben II-E | (2) | PROPYLENE GLYCOL, DIAZOLIDINYL UREA, METHYLPARABEN, PROPYLPARABEN | 0.80 |
| Water, demineralized | | AQUA (WATER) | ad 100 |
| B | | | |
| RonaCare ® AP | (1) | BIS-ETHYLHEXYL HYDROXYDIMETHOXY BENZYLMALONATE | 1.00 |
| Abil EM 90 | (3) | CETYL PEG/PPG-10/1 DIMETHICONE | 3.00 |
| Abil Wax 9810 P | | C24-28 ALKYL METHICONE | 2.00 |
| Wax white | (1) | CERA ALBA (BEESWAX) | 0.50 |
| Cutina HR | (4) | HYDROGENATED CASTOR OIL | 0.50 |
| Cetiol ® 868 | (4) | ETHYLHEXYL STEARATE | 7.00 |
| Arlamol ™ HD-LQ-(RB) | (5) | ISOHEXADECANE | 4.00 |
| C | | | |
| Mirasil CM 5 | (6) | CYCLOPENTASILOXANE | 4.00 |
| Dow Corning 246 Fluid | (7) | CYCLOHEXASILOXANE, CYCLOPENTASILOXANE | 2.00 |
| Wacker Belsil CM 040 | (8) | CYCLOPENTASILOXANE | 5.00 |
| D | | | |
| Fragrance (q.s.) | | PARFUM | 0.20 |
| Mixture 1 | | SERINE, CALCIUM LACTATE, PCA, ARGININE, HISTIDINE | 1.00 |

Procedure:

Heat phases A and B to 80° C. Add phase C to phase B. Stir phase A into phase B/C. Homogenize. Cool down while stirring. Add phase D.

Homogenize under 30° C. Stir to room temperature.

Source of Supply:

(1) Merck KGaA, Darmstadt, Germany/EMD Performance Materials; (2) ISP Global Technologies; (3) Evonik Nutrition & Care GmbH; (4) BASF SE; (5) Croda; (6) Azelis Germany GmbH; (7) Biesterfeld; (8) Wacker Chemie AG

Example 6: Anti-Aging Gel

| Ingredients | | INCI (CTFA) | [%] |
|---|---|---|---|
| A | | | |
| Water, demineralized | | AQUA (WATER) | ad 100 |
| Preservatives (q.s.) | | | 0.00 |
| 1,3-Butanediol | (1) | BUTYLENE GLYCOL | 4.00 |
| RonaCare ® Ectoin | (1) | ECTOIN | 0.30 |
| Mixture 1 | | SERINE, CALCIUM LACTATE, PCA, ARGININE, HISTIDINE | 1.00 |
| B | | | |
| Sepinov P88 | (2) | SODIUM ACRYLATE/ ACRYLOYLDIMETHYLTAURATE/ DIMETHYLACRYLAMIDE CROSSPOLYMER | 1.50 |
| Soybean Oil | (3) | GLYCINE SOJA (GLYCINE SOJA (SOYBEAN) OIL) | 2.50 |
| Tegosoft ® TN | (4) | C12-15 ALKYL BENZOATE | 2.50 |
| C | | | |
| Fragrance (q.s.) | | PARFUM | 0.00 |
| RonaCare ® Cyclopeptide-5 | (1) | AQUA (WATER), ALCOHOL, LECITHIN, ECTOIN, CYCLOTETRAPEPTIDE-24 AMINOCYCLOHEXANE CARBOXYLATE | 3.00 |
| D | | | |
| RonaCare ® Luremin ® | (1) | SORBITOL, DIHYDROXY METHYLCHROMONE | 1.00 |
| Water, demineralized | | AQUA (WATER) | 10.00 |

Procedure:

Add phase A slowly with vigorous stirring to phase B. Homogenize.

Add phase C. Finally add the dispersed phase D under stirring.

Adjust pH value with NaOH to pH 5.0-5.5.

Source of Supply:

(1) Merck KGaA, Darmstadt, Germany/EMD Performance Materials; (2) Seppic GmbH; (3) Gustav Heess GmbH; (4) Evonik Nutrition & Care GmbH

Example 7: Silky Face Serum (W/Si)

| Ingredients | | INCI (CTFA) | [%] |
|---|---|---|---|
| A | | | |
| RonaCare ® Troxerutin | (1) | TROXERUTIN | 0.50 |
| Water, demineralized | | AQUA (WATER) | ad 100 |
| Complexing agent (q.s.) | | | 0.00 |
| Mixture 1 | | SERINE, CALCIUM LACTATE, PCA, ARGININE, HISTIDINE | 1.00 |
| B | | | |
| Glycerol 85% | (1) | GLYCERIN, AQUA (WATER) | 5.00 |
| Natrosol 250 H | (2) | HYDROXYETHYLCELLULOSE | 0.60 |

-continued

| Ingredients | | INCI (CTFA) | [%] |
|---|---|---|---|
| C | | | |
| Lubrajel Oil | (3) | PVM/MA COPOLYMER, PROPYLENE GLYCOL, GLYCERYL POLYMETHACRYLATE | 33.00 |
| Euxyl® PE 9010 | (4) | PHENOXYETHANOL, ETHYLHEXYL GLYCERIN | 1.00 |
| D | | | |
| Dow Corning 7-3100 Gum Blend HIP Emulsion | (5) | CYCLOPENTASILOXANE, DIMETHICONOL, LAURETH-LAURETH-4 | 40.00 |

Procedure:

Phase A: Dissolve RonaCare® Troxerutin in water ad Mixture 1 and adjust to pH 5.5.

Phase B: Pre-disperse HYDROXYETHYLCELLULOSE in Glycerin.

Add phase B to phase A while stirring, and let swell.

Add phase C, and afterwards phase D slowly.

Source of Supply:

(1) Merck KGaA, Darmstadt, Germany/EMD Performance Materials; (2) Aqualon GmbH; (3) Ashland; (4) Schülke & Mayr GmbH; (5) Biesterfeld Example 8: Rinse-Off Mask

| Ingredients | | INCI (CTFA) | [%] |
|---|---|---|---|
| A | | | |
| Matalgin PLF | (1) | DIATOMACEOUS EARTH, ALGIN, CALCIUM SULFATE, TETRASODIUM PYROPHOSPHATE | 50.00 |
| Tapioca Pure | | TAPIOCA STARCH | 24.50 |
| Jojoba Oil | | JOJOBA OIL | 3.00 |
| A1 | | | |
| (S)-Lactic acid about 90% | (2) | LACTIC ACID, AQUA (WATER) | 0.45 |
| Mixture 1 | | SERINE, CALCIUM LACTATE, PCA, ARGININE, HISTIDINE | 1.00 |
| Water, demineralized | | AQUA (WATER) | ad 100 |
| B | | | |
| Cornflower Extract | | MALTODEXTRIN, CENTAUREA CYANUS EXTRACT | 9.00 |
| RonaFlair® White Sapphire | (2) | ALUMINA (OR ALTERNATIVELY: SYNTHETIC SAPPHIRE) | 9.00 |

Procedure:

Mix Matalgin PLF and Tapioca Pure 2 times 10 seconds in a blender. Add jojoba oil and mix again 2 times for 10 seconds. Add phase A1 and mix 2 times for 10 seconds. Add phase B and mix 2 times for 10 seconds.

Source of Supply:

(1) Alliance Gums & Industries; (2) Merck KGaA, Darmstadt, Germany/EMD Performance Materials Example 9: Soothing Face Mask for Sensitive Skin

| Ingredients | | INCI (CTFA) | [%] |
|---|---|---|---|
| A | | | |
| RonaCare® Ectoin | (1) | ECTOIN | 1.00 |
| RonaCare® Nicotinamide | (1) | NIACINAMIDE | 2.00 |
| Carbopol® Ultrez 21 | (2) | ACRYLATES/C10-30 ALKYL ACRYLATE CROSSPOLYMER | 0.20 |
| Glycerol 85% | (1) | GLYCERIN, AQUA (WATER) | 5.00 |
| Rhodicare XC | (3) | XANTHAN GUM | 0.30 |
| Water, demineralized | | AQUA (WATER) | ad 100 |
| Titriplex® III | (1) | DISODIUM EDTA | 0.05 |
| Montanov™ L | (4) | C14-22 ALCOHOLS, C12-20 ALKYL GLUCOSIDE | 4.00 |
| Montanov™ 14 | (4) | MYRISTYL ALCOHOL, MYRISTYL GLUCOSIDE | 2.00 |
| B | | | |
| RonaCare® AP | (1) | BIS-ETHYLHEXYL HYDROXYDIMETHOXY BENZYLMALONATE | 1.00 |
| RonaCare® Bisabolol nat. | (1) | BISABOLOL | 0.50 |
| Cetyl Alcohol | (1) | CETYL ALCOHOL | 1.00 |
| LIPOCIRE A SG | (2) | C10-18 TRIGLYCERIDES | 3.00 |
| Cetiol® SB 45 | (5) | *BUTYROSPERMUM PARKII* BUTTER (*BUTYROSPERMUM PARKII* (SHEA) BUTTER) | 5.00 |
| Mango butter XNE003 | (6) | *MANGIFERA INDICA* SEED BUTTER (*MANGIFERA INDICA* (MANGO) SEED BUTTER) | 5.00 |
| Crodamol ISIS-LQ-(MV) | (7) | ISOSTEARYL ISOSTEARATE | 5.00 |
| C | | | |
| Sodium Hydroxide, 10% | (1) | AQUA (WATER), SODIUM HYDROXIDE | 0.50 |
| D | | | |
| RonaFlair® Boroneige® SF-3 | (1) | BORON NITRIDE | 2.00 |
| E | | | |
| Euxyl PE 9010 | (8) | PHENOXYETHANOL, ETHYLHEXYL GLYCERIN | 1.00 |
| Mixture 1 | | SERINE, CALCIUM LACTATE, PCA, ARGININE, HISTIDINE | 1.00 |

Procedure:

Disperse Carbopol Ultrez 21 in the water and stir until homogeneous. Add the xanthan gum premixed with glycerin and stir until homogeneous. Add the active ingredients and stir until homogeneous. Add the Montanov and heat A to 80° C.

Prepare phase B and heat B to 80° C. Emulsion: pour B into A under high stirring. Neutralize with C and homogenize and adjust final pH 5.5

At T<60° C. add D and stir until homogeneous. Slowly cool the cream under gentle stirring. At T<35° C. add E adjust finally to pH 5.5 and stir until homogeneous.

Source of Supply:

(1) Merck KGaA, Darmstadt, Germany/EMD Performance Materials; (2) Gattefosse (Deutschland) GmbH; (3)

SACI CFPA; (4) Seppic; (5) BASF SE; (6) Greentech SA; (7) Croda; (8) Schulke & Mayr GmbH Brief Description of the Drawings FIG. 1 shows the relative fluorescence of the measured media as described in Example 1.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A mixture consisting of serine, arginine, histidine, pyrrolidinone-5-carboxylic acid and calcium lactate or its hydrate,
    wherein serine is present in 25 to 35% by weight, arginine is present in 5 to 10% by weight, histidine is present in 5 to 10% by weight, pyrrolidinone-5-carboxylic acid is present in 10 to 30% by weight and the calcium lactate or its hydrate is present in 25 to 35% by weight, and wherein the combined total amounts add to 100% by weight.

2. The mixture according to claim 1, consisting of serine, arginine, histidine, pyrrolidinone-5-carboxylic acid and calcium lactate hydrate.

3. The mixture according to claim 1, which is a powder mixture.

4. A formulation, consisting of the mixture according to claim 1 and a solvent.

5. A cosmetic or dermatological composition, consisting of a mixture of serine, arginine, histidine, pyrrolidinone-5-carboxylic acid and calcium lactate or its hydrate,
    wherein serine is present in 25 to 35% by weight, arginine is present in 5 to 10% by weight, histidine is present in 5 to 10% by weight, pyrrolidinone-5-carboxylic acid is present in 10 to 30% by weight and the calcium lactate or its hydrate is present in 25 to 35% by weight, and wherein the combined total amounts add to 100% by weight.

6. A method to increase cellular availability of calcium in living cells of the epidermis, comprising applying to the skin the mixture of claim 1.

* * * * *